(12) United States Patent
Kennington

(10) Patent No.: US 10,048,191 B2
(45) Date of Patent: Aug. 14, 2018

(54) METHODS AND APPARATUS FOR REAL-TIME DETECTION AND CLEARING OF A CLOG

(71) Applicant: Intellicyt, Albuquerque, NM (US)

(72) Inventor: Aaron B. Kennington, Albuquerque, NM (US)

(73) Assignee: Intellicyt, Albuquerque, NM (US)

( * ) Notice: Subject to any disclaimer, the term of this patent is extended or adjusted under 35 U.S.C. 154(b) by 0 days.

(21) Appl. No.: 15/411,366

(22) Filed: Jan. 20, 2017

(65) Prior Publication Data

US 2017/0138836 A1 May 18, 2017

Related U.S. Application Data

(62) Division of application No. 14/328,755, filed on Jul. 11, 2014, now Pat. No. 9,551,644.

(51) Int. Cl.
*A61B 6/00* (2006.01)
*G01N 15/14* (2006.01)

(52) U.S. Cl.
CPC . *G01N 15/1404* (2013.01); *G01N 2015/1418* (2013.01)

(58) Field of Classification Search
CPC .. G01N 15/1475; G01N 15/1404; G01N 1/34; G01N 2035/1048
USPC ........................................................ 250/581
See application file for complete search history.

(56) References Cited

U.S. PATENT DOCUMENTS

| | | | | |
|---|---|---|---|---|
| 5,395,588 A | * | 3/1995 | North, Jr. ........... | G01N 15/1404 422/67 |
| 5,776,781 A | * | 7/1998 | Vardanega ............... | B01L 1/04 209/3.1 |
| 5,939,326 A | * | 8/1999 | Chupp ................. | B01F 5/0453 422/63 |
| 6,878,556 B2 | | 4/2005 | Sklar et al. | |
| 6,890,487 B1 | | 5/2005 | Sklar et al. | |
| 7,368,084 B2 | | 5/2008 | Sklar et al. | |
| 7,842,244 B2 | | 11/2010 | Sklar et al. | |
| 8,021,872 B2 | | 9/2011 | Sklar et al. | |
| 8,268,571 B2 | | 9/2012 | Sklar et al. | |
| 2006/0256338 A1 | * | 11/2006 | Gratton ............. | G01N 15/1463 356/417 |

(Continued)

FOREIGN PATENT DOCUMENTS

WO 2010/005617 1/2010

*Primary Examiner* — Taeho Jo
(74) *Attorney, Agent, or Firm* — McDonnell Boehnen Hulbert & Berghoff LLP

(57) ABSTRACT

A flow cytometer apparatus and methods for detecting and clearing a clog therein are disclosed. An example method for detecting a clog may include (i) detecting, via a fault detection system of a flow cytometer, a first plurality of events associated with a first aliquot from a first sample well, (ii) determining a count of the first plurality of events associated with the first aliquot, (iii) determining whether the count of the first plurality of events is below a minimum count tolerance and (iv) (a) if the count of the first plurality of events is below the minimum count tolerance, then determining that the flow cytometer has a clog, (b) if the count of the first plurality of events is equal to or above the minimum count tolerance, then detecting a second plurality of events associated with a second aliquot from a second sample well.

14 Claims, 7 Drawing Sheets

(56) References Cited

U.S. PATENT DOCUMENTS

| | | | |
|---|---|---|---|
| 2008/0092961 A1* | 4/2008 | Bair | F04B 23/04 137/565.11 |
| 2009/0109432 A1* | 4/2009 | Olson | G01N 21/05 356/244 |
| 2010/0015601 A1* | 1/2010 | Gilmore | G01N 1/2202 435/6.16 |
| 2010/0126935 A1* | 5/2010 | Echizen | B01D 61/025 210/652 |
| 2010/0197512 A1 | 8/2010 | Trinkle et al. | |
| 2010/0319786 A1* | 12/2010 | Bair | F04B 23/04 137/15.01 |
| 2012/0061584 A1 | 3/2012 | Trinkle et al. | |
| 2012/0070818 A1* | 3/2012 | Rowlen | G01N 15/14 435/3 |
| 2012/0141898 A1* | 6/2012 | Tanaka | H01M 8/04097 429/431 |
| 2012/0220022 A1* | 8/2012 | Ehrlich | G01N 15/14 435/286.2 |
| 2012/0309635 A1 | 12/2012 | Trinkle et al. | |
| 2013/0210672 A1* | 8/2013 | Sklar | G01N 15/1459 506/12 |
| 2013/0316336 A1* | 11/2013 | Matsui | G01N 35/1095 435/6.1 |
| 2013/0337472 A1* | 12/2013 | Doxsey | C07K 14/705 435/7.23 |
| 2014/0268102 A1* | 9/2014 | Shah | G01N 15/1459 356/39 |
| 2014/0308659 A1* | 10/2014 | Alburty | G01N 1/4077 435/5 |
| 2014/0322710 A1* | 10/2014 | Craighead | B01L 3/502761 435/6.11 |
| 2015/0192574 A1* | 7/2015 | Cottier | G01N 33/5302 436/501 |
| 2015/0275264 A1* | 10/2015 | Buzatu | C12Q 1/06 435/34 |
| 2015/0300940 A1* | 10/2015 | Bair | G01N 15/1404 73/863.03 |

\* cited by examiner

METHODS AND APPARATUS FOR REAL-TIME DETECTION AND CLEARING OF A CLOG

RELATED APPLICATION

This application is a divisional application of U.S. patent application Ser. No. 14/328,755 filed Jul. 11, 2014, incorporated by reference herein in its entirety.

BACKGROUND

Unless otherwise indicated herein, the materials described in this section are not prior art to the claims in this application and are not admitted to be prior art by inclusion in this section.

Flow cytometry is a technology employed in cell counting, cell sorting, biomarker detection and protein engineering, for example, conducted by suspending cells in a stream of fluid and passing them by an electronic detection apparatus. Flow cytometry allows simultaneous multiparametric analysis of the physical and/or chemical characteristics of up to thousands of particles per second. A flow cytometer may be capable of actively separating and isolating particles that have properties of interest and may permit automated quantification of set parameters.

SUMMARY

Example embodiments provide flow cytometer apparatus and methods for detecting and/or clearing of a clog in the flow cytometer apparatus. The apparatus and methods may beneficially permit detection of clog via a fault detection system that allows data collection to pause and then resume upon the clearing of the clog. The method for clearing the clog advantageously permits clog removal without the need to identify the clog's location in the flow cytometer apparatus such that the flow cytometer apparatus need not be taken apart. In addition, the clog detection and remediation methods may be automated and any clog may be cleared without the need for operator intervention.

Thus, in one aspect, a flow cytometer apparatus is provided, including (i) a flow cell having a first end and a second end, (ii) a sample fluidic pathway having a first end and a second end, where the second end of the sample fluidic pathway is coupled to the first end of the flow cell, (iv) a sample probe coupled to the first end of the sample fluidic pathway, (v) a sample pump in fluid communication with the sample fluidic pathway, (vi) a waste line having a first end and a second end, where the first end of the waste line is coupled to the flow cell and (vii) a waste pump in fluid communication with the waste.

In a second aspect, a method for detecting a clog in a flow cytometer apparatus is provided including the steps of (i) detecting, via a fault detection system of a flow cytometer, a first plurality of events associated with a first aliquot from a first sample well, (ii) determining, via the fault detection system, a count of the first plurality of events associated with the first aliquot, (iii) determining, via the fault detection system, whether the count of the first plurality of events is below a minimum count tolerance and (iv) (a) if the count of the first plurality of events is below the minimum count tolerance, then determining, via the fault detection system, that the flow cytometer has a clog, (b) if the count of the first plurality of events is equal to or above the minimum count tolerance, then detecting, via the fault detection system, a second plurality of events associated with a second aliquot from a second sample well.

In a third aspect, a method for clearing a clog from a flow cytometer apparatus is provided including the steps of (i) providing a flow cytometer system comprising (a) a flow cell having a first end and a second end, (b) a sample fluidic pathway having a first end and a second end, where the second end of the sample fluidic pathway is coupled to the first end of the flow cell, (c) a sample probe coupled to the first end of the sample fluidic pathway, (d) a sample pump in fluid communication with the sample fluidic pathway, (e) a waste line having a first end and a second end, where the first end of the waste line is coupled to the flow cell and (f) a waste pump in fluid communication with the waste line, (ii) activating the waste pump to apply negative pressure to one or more of the waste line, the flow cell, the sheath fluidic pathway and the sample fluidic pathway, (iii) activating the sample pump and (iv) cycling the sample probe into and out of a decontamination solution reservoir and driving a decontamination fluid, via the sample pump, through one or more of the flow cell, the sample fluidic pathway and the waste line, thereby clearing a clog.

These as well as other aspects, advantages, and alternatives, will become apparent to those of ordinary skill in the art by reading the following detailed description, with reference where appropriate to the accompanying drawings.

DETAILED DESCRIPTION

Figure 1:
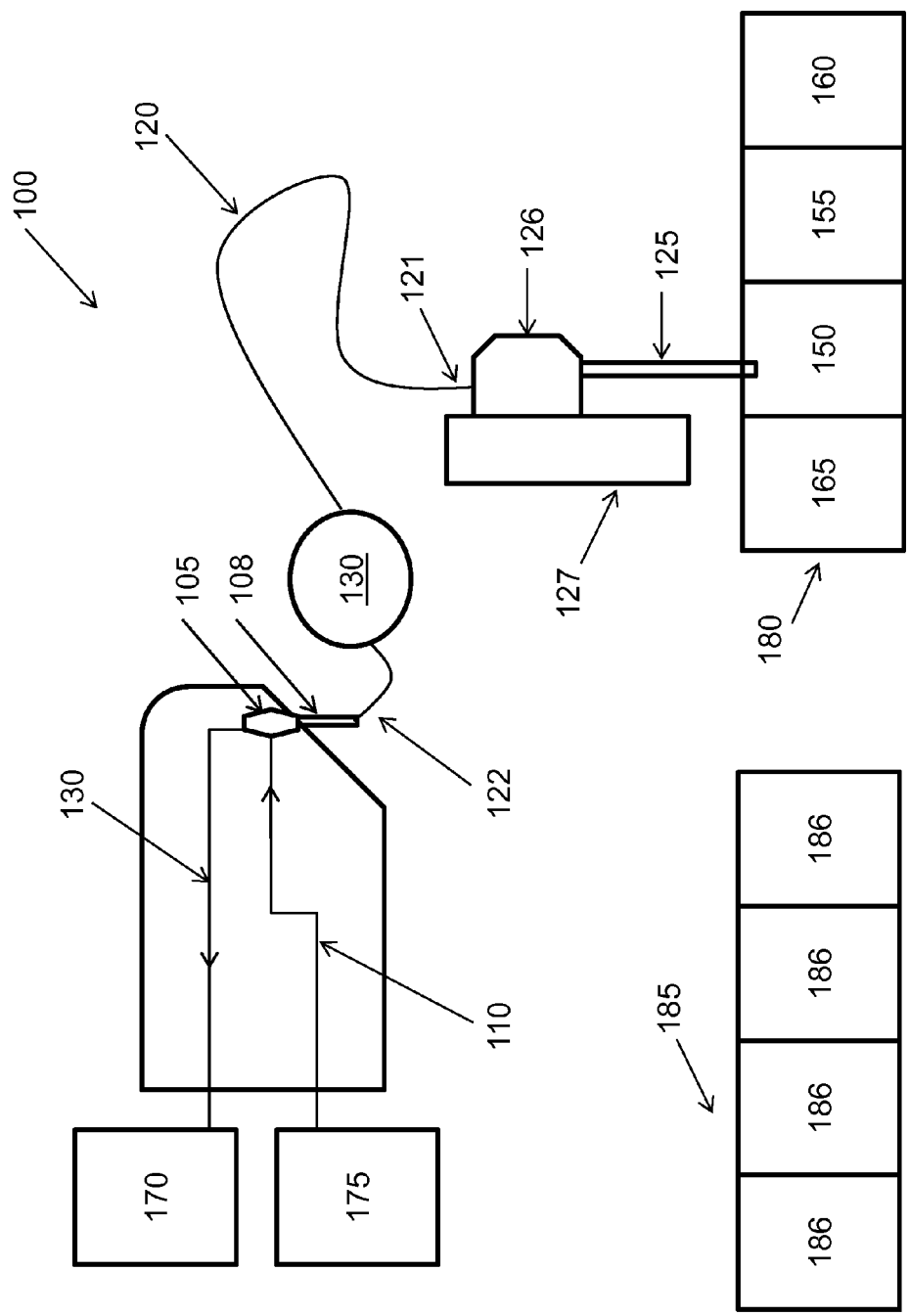
FIG. 1 is a schematic view of a flow cytometer apparatus and series of washing reservoirs, according to one example embodiment.

Example flow cytometer apparatus and methods for detecting and/or clearing of a clog in the flow cytometer apparatus are described herein. Any example embodiment or feature described herein is not necessarily to be construed as preferred or advantageous over other embodiments or features. The example embodiments described herein are not meant to be limiting. It will be readily understood that certain aspects of the disclosed methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, "about" means+/−5%.

As used herein "well" means structure which contains a sample to be analyzed, a control or an aliquot of marker particles.

As used herein "microplate" and "plate" refer to a structure capable of holding one or more samples to be analyzed or aliquot of marker particles.

As used herein "sample" refers to any quantity of liquid which may contain particles of interest or marker particles that are detectable by a particle analyzer. More specifically a sample may include a fluid solution or suspension containing particles of interest or marker particles to be detected and/or analyzed using a method and/or apparatus disclosed herein. The particles of interest in a sample may be tagged, such as with a fluorescent tag. The particles of interest may also be bound to a bead, a receptor, or other useful protein or polypeptide, or may just be present as free particles, such as particles found naturally in a cell lysate, purified particles from a cell lysate, particles from a tissue culture, etc. The sample may include chemicals, either organic or inorganic, used to produce a reaction with the particles of interest. When the particles of interest are biomaterials, drugs may be added to the samples to cause a reaction or response in the biomaterial particles. The chemicals, drugs or other additives may be added to and mixed with the samples when the samples are in sample source wells or the chemicals, drugs or other additives may be added to the samples in the fluid flow stream after the samples have been uptaken by the autosampler.

As used herein, the term "biomaterial" refers to any organic material obtained from an organism, either living or dead. The term "biomaterial" also refers to any synthesized biological material such as synthesized oligonucleotides, synthesized polypeptides, etc. The synthesized biological material may be a synthetic version of a naturally occurring biological material or a non-naturally occurring biological made from portions of naturally occurring biological materials, such as a fusion protein, or two biological materials that have been bound together, such as an oligonucleotide, such as DNA or RNA, bound to a peptide, either covalently or non-covalently, that the oligonucleotide does not normally bind to in nature.

As used herein, the term "oligonucleotide" refers to any oligonucleotide, including double and single-stranded DNA, RNA, PNAs (peptide nucleic acids) and any sequence of nucleic acids, either natural or synthetic, derivatized or underivatized.

As used herein, "peptide" refers to all types of peptides and conjugated peptides including: peptides, proteins, polypeptides, protein sequences, amino acid sequences, denatured proteins, antigens, oncogenes and portions of oncogenes.

As used herein, the term "organism" refers not only to animals, plants, bacteria, viruses, etc. but also to cell cultures, reproduced oligonucleotides, etc. made from organic material obtained from animals, plants, bacteria, viruses, etc.

As used herein, the term "drug" refers to any type of substance that is commonly considered a drug. A drug may be a substance that acts on the central nervous system of an individual, eg a narcotic, hallucinogen, barbiturate, or a psychotropic drug. For the purposes of the present invention, a drug may also be a substance that kills or inactivates disease-causing infectious organisms. In addition, a drug may be a substance that affects the activity of a specific cell, bodily organ or function. A drug may be an organic or inorganic chemical, a biomaterial, etc.

As used herein, an "aliquot" is a sip of a sample taken from a well via a probe of a flow cytometer.

As used herein, the term "fluidic pathway" or "conduit" refers to device such as a tube, channel, etc. through which a fluid stream flows. A fluidic pathway may be composed of several separate devices, such as a number of connected or joined pieces of tubing or a single piece of tubing, alone or in combination with channels or other different devices. In various embodiments, a fluidic pathway may include any tube that may be used with a peristaltic pump that has compression characteristics that allow a peristaltic pump to move samples separated by a separation gas or aliquots of marker particles through the tube at a speed of at least 6 samples per minute without causing adjacent samples to mix with each other.

As used herein "marker particles" may include control particles, beads or microbeads and further refers to one or more particles detectable by a flow cytometer system (for example a system as described in U.S. Pat. No. 6,878,556 and WO2010005617) that may uptake from a sample container an aliquot of a sample suspected of having therein particles of interest to be analyzed.

In one embodiment, introducing the plurality of samples into a conduit or fluidic pathway includes uptaking each of the plurality of samples from a respective sample container. For example, the respective sample container may be a microplate having rows and columns of sample wells for holding samples to be tested.

According to one embodiment, fluid gaps are gas gaps, for example air gaps.

According to another embodiment, flowing the plurality of samples includes moving the samples with a pump, gravity, acoustic means, microcapillary action, pressurization or any combination thereof.

According to still another embodiment, detecting particles of interest when present in the detector zone depends on the optical and/or physical characteristic of interest selected for the particles of interest. According to a further embodiment detecting marker particles may depend on the optical and/or physical characteristics selected for the marker particles. For example, marker particles may be selected based upon optical and/or physical characteristics which may be the same or different from the optical and/or physical characteristics of the particles of interest.

In one embodiment, the system may include a sample to be analyzed which may be transported from a sample well to a detector of the flow cytometer via a conduit or fluidic pathway. The sample to be analyzed may be taken up from the sample well via a probe. In between samples, the probe may uptake a separation gas. Multiple samples may be transported in the conduit sequentially. The multiple samples may be separated from each other via fluid gaps (e.g. air) and a plurality of samples to be analyzed may be moved along the conduit or fluidic pathway to the detector thereby creating a flowing stream of samples to be analyzed. Particles of interest within the sample to be analyzed may flow in a flow cell and pass an illumination source in a detector zone. The demarcation or delineation between the plurality of samples to be analyzed in the flowing stream within the conduit or fluidic pathway may be the fluid gap positioned between each one of the plurality of samples to be analyzed. For example, a first sample to be analyzed is separated from a second sample to be analyzed via one or more air gaps according to one embodiment of the present invention.

From a sample to be analyzed, a population of particles may be identified based upon their optical/physical characteristics such as light scatter, emission properties, size, but not limited thereto. Particles of interest from the plurality of samples to be analyzed sharing the desired characteristic may be detected by the detector in the detector zone as the particles of interest pass between the detector and a light source that provides a light path that strikes the detector within the detector zone (e.g., a laser interrogation point). As the samples to be analyzed pass the detector (e.g. photomultiplier tube) of the particle analyzer, samples having particles of interest with optical and/or physical characteristics that are within the desired/set optical and/or physical characteristics will be identified as an event (particle having or producing the desired optical and/or physical properties for analysis). The air gaps between the samples do not contain particles of interest that will be recorded as an event. Therefore, a graph of the data points of fluorescence sensed versus time for a series of samples analyzed using a flow cytometer may form distinct groups, each aligned with the time that a sample containing particles passes through the laser interrogation or detection point. In order to detect the presence of each of two or more different types of samples, in a heterogeneous plurality of samples, each of the two or more different types of samples may be tagged with different fluorescent tags, different amounts of a single tag or some combination of different tags and different amount of a single tag. In such a case, the groupings of data points may vary vertically on a fluorescence versus time graph, depending on which type of sample is being sensed. As with the case of sensing a single type of sample, each sensed sample will exhibit a group of data points aligned with the time that the sample passes through the laser interrogation point.

In another embodiment, the marker particles may be comingled with the sample to be analyzed and the apparatus and method may utilize marker particles to identify the location within the sample stream of a sample to be analyzed. In an embodiment in which marker particles are not present, the delineation of each sample to be analyzed in the sample stream may be easily identified when particles of interest in the samples to be analyzed are relatively similar in terms of their concentration and/or other optical and/or physical characteristics. If the multiple samples to be analyzed in the conduit or fluidic pathway are different with respect to the particles of interest—for example, if there are very few particles of interest in some of the samples to be analyzed, or if there are large gaps inserted between the air gaps where a sample to be analyzed would be expected but for an instrument malfunction—the location of the sample to be analyzed in the data stream may become problematic in the absence of marker particles.

In one embodiment in which the marker particles are comingled with a sample to be analyzed. The flow cytometric properties of the marker particles may be different from those of the particles of interest within the samples to be analyzed. The difference in the optical and/or physical characteristics of the marker particles along with the fact that there may be known numbers of marker particles comingled with each sample to be analyzed may allow a user to delineate the location of the sample to be analyzed in the data stream even if there are no particles of interest in the sample to be tested other than the marker particles.

In various embodiments, marker particles may be added to a well containing sample or a non-sample containing well. The marker particles may have a known characteristic such as known size, fluorescent intensity, forward light scatter and side light scatter for example. However, other characteristics that are well known in the art for detecting and characterizing particles may be useful in a particle analyzer such as the particle analyzer disclosed in U.S. Pat. No. 6,878,556 may also be useful. For example, in one embodiment, the marker particles may be introduced between samples, and thus demarcate the anticipated beginning location in the flowing stream of a sample to be analyzed prior to the sample to being analyzed entering the detector zone of the particle analyzer. Once the bolus of sample to be analyzed moves past the detector zone, a subsequent bolus of marker particles in the conduit may move past the detector zone, indicating the anticipated ending location in the flowing stream of a sample to be analyzed. These marker particles have known physical and/or optical characteristics, including emission spectra, intensity, shape, size, which are captured by the particle analyzer (e.g. flow cytometer). The marker particles may be added in known positions relative to the samples to be analyzed in the flowing stream. A fault detection system may then utilize the characteristics and the temporal position within the flowing stream of the marker particles to determine the anticipated location of a sample to be analyzed in the flowing stream and/or data stream and to determine whether there is a clog in the flow cytometer system.

In one embodiment, in which the samples to be analyzed and marker particles alternate in the conduit, the time boundaries of each sample to be analyzed when present in the detector zone may be set based on the lowest number of events associated with a histogram developed based upon the marker particles in a given aliquot. Specifically, boundaries representing time gates may be determined before and after a marker particle histogram to represent the location for the end point of a first sample and the starting point of a subsequent second sample, respectively, to be analyzed when present in the detector zone. The histograms may be developed in real-time during sample flow and analysis through the detector zone to aid in clog detection and sample analysis. In addition, the correlation of a histogram back to the x-y coordinates of a sample container (for example, the position of a well on a plate) may be determined based upon the timing and sampling order used in the sampling process. Since the samples to be analyzed and marker particles alternate in the conduit or fluidic pathway, each histogram peak of a sample to be analyzed may appear at a unique time period and may be assigned to the sample well identified by the marker particle data.

One advantage of this method may be that in experiments performed with an autosampler sampling system as described herein, there are often cases when individual wells of the plate may contain no sample events due to sampling error or effects of chemical treatment of the sample. Moreover, it is not typically known in advance which wells may be empty of test sample events. With this method, wells that contain no test sample events may be accurately identified via the marker particle histograms.

One embodiment provides delineation between samples to be analyzed when the samples to be analyzed are acquired in a flowing stream separated by air gaps, for example. In this embodiment, marker particles may be commingled in the same wells as the sample particles of interest. For example, marker particles may represent about 1-2% of the total particles in a given sample. As noted above, there may often be cases when an individual well of the plate contains no particles and therefore no events to detect by the particle analyzer due to sampling error or effects of chemical treatment of the sample. Moreover, it may not be known in advance which wells will be empty of particles to be analyzed/events. With this method, wells that contain no test sample events can be accurately identified via the marker particle peaks.

In one aspect, the invention provides a flow cytometer apparatus, comprising:

a flow cell having a first end and a second end;

a sample fluidic pathway having a first end and a second end, wherein the second end of the sample fluidic pathway is coupled to the first end of the flow cell;

a sample probe coupled to the first end of the sample fluidic pathway;

a sample pump in fluid communication with the sample fluidic pathway;

a waste line having a first end and a second end, wherein the first end of the waste line is coupled to the flow cell; and a waste pump in fluid communication with the waste line.

Figure 2:
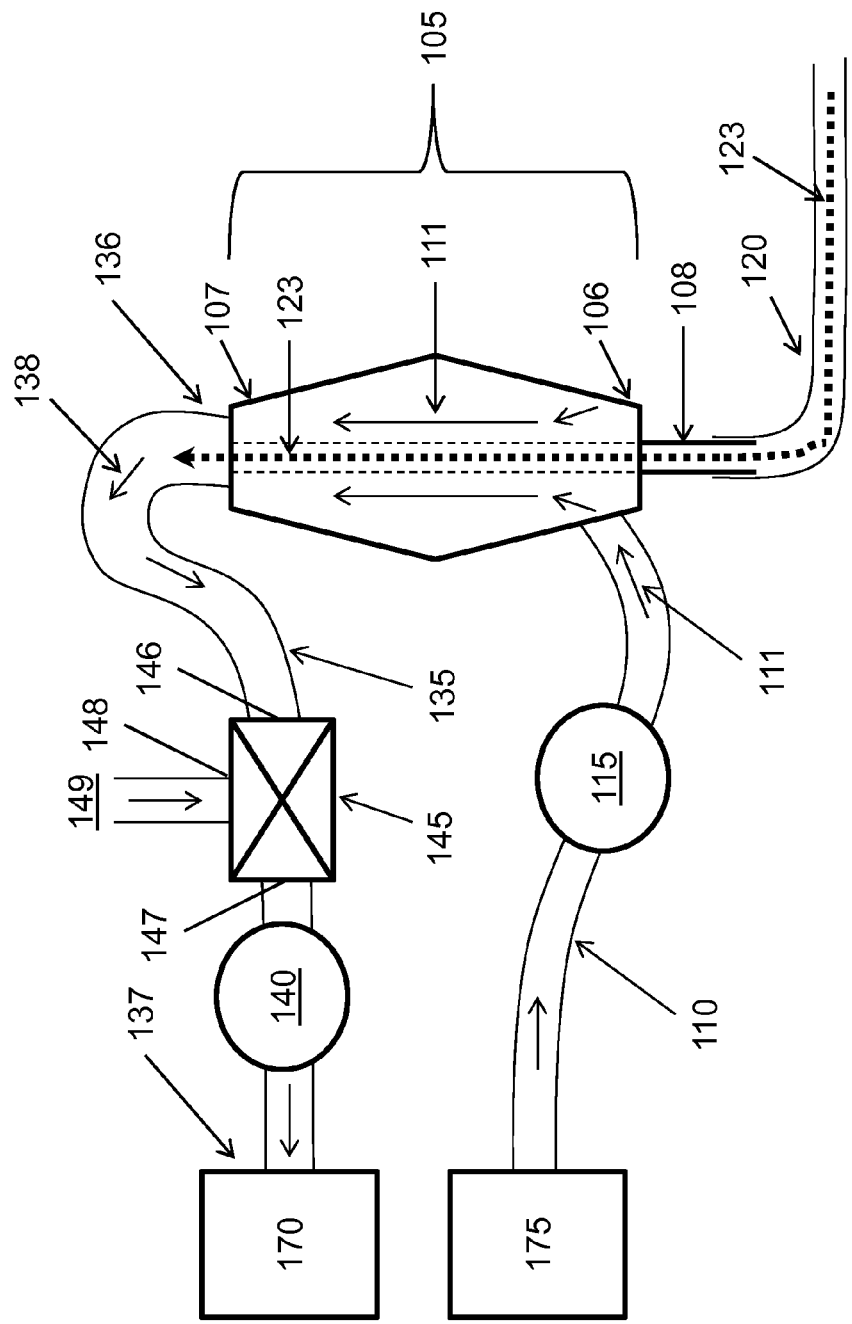
FIG. 2 is a detail view of a flow cell and flow cytometer engine of the flow cytometer apparatus of FIG. 1, according to one example embodiment.

Referring now to FIGS. 1-2, a flow cytometer apparatus 100 is shown including a flow cell 105 having a first end 106 and a second end 107. A sheath fluidic pathway 110 may be coupled to the first end 106 of the flow cell 105 and a sheath pump 115 may be in fluid communication with the sheath fluidic pathway 110. In one embodiment, the sheath fluidic pathway 110 may be coupled to a sheath fluid reservoir 175 that is configured to hold sheath fluid 111. During testing operations performed by the flow cytometer apparatus 100, the sheath pump 115 may drive the sheath fluid 111 from the sheath fluid reservoir 175 through the sheath fluidic pathway 110 and through the flow cell 105.

The flow cytometer apparatus 100 also includes a sample fluidic pathway 120 having a first end 121 and a second end 122. The second end 122 of the sample fluidic pathway 120 is coupled to the first end 106 of the flow cell 105. The flow cytometer apparatus 100 further includes a sample probe 125. An example probe may include a 0.01 inch ID, 1/16 inch OD stainless steel needle compatible with HPLC ferrule fittings. In one embodiment, in order to reduce carryover of samples between wells, the probe 125 may have a conical tip. In another embodiment, silicone or other hydrophobic agent may coat the tip of the sampling probe 125 to help minimize sample carryover. In an alternative embodiment, the entire probe 125 may be made of a hydrophobic material to reduce carryover. Suitable hydrophobic materials for use in the coating or for making the entire hydrophobic probe include: Teflon® (poly(tetrafluoroethylene) (PTFE)), Kynar® (polyvinylidene fluoride), Tefzel® (ethylene-tetrafluoroethylene copolymer), tetrafluoroethylene-perfluoroalkyl vinyl ether copolymer resin (PFA), a tetrafluoroethylene-hexafluoropropylene copolymer (EFP), polyether ether ketone (PEEK), etc.

In one embodiment, the sample probe 125 may be coupled to a probe holder 126. In one embodiment, the flow cytometry apparatus 100 may include a conventional autosampler 127, such as the Gilson 215 liquid manager. The probe holder 126 of the autosampler 127 may take the form of an adjustable arm. As probe holder 126 moves side to side and up and down, probe 125 is lowered into individual source wells 186 of a well plate 185 to obtain a sample that has been tagged with a fluorescent tag to be analyzed using the flow cytometry apparatus 100. In turn, the sample probe 125 is coupled to the first end 121 of the sample fluidic pathway 120, and a sample pump 130 is in fluid communication with the sample fluidic pathway 120. In operation, the sample probe 125 may take up a sample from a well in a well-plate, for example, and then advance the sample into the sample fluidic pathway 120. The sample pump 130 may then drive a sample stream 123 through the sample fluidic pathway 120 to a sample inlet port 108 and through the flow cell 105. In one embodiment, the flow cell 105 may include a laser interrogation device that may examine individual samples flowing from flow cell 105 at a laser interrogation point. Once the sample stream 123 enters the flow cell 105, then the sheath fluid 111 flowing through the flow cell 105 may aid in hydrodynamic focusing of the samples in the center of the flow cell 105. As shown, the sample stream 123 may include a series of samples each separated by an air gap. These air gaps may be formed by allowing sample probe 125 to intake air in between intaking sample material from each of sample wells 186.

In addition, the flow cytometer apparatus 100 includes a waste line 135 having a first end 136 and a second end 137. The first end 136 of the waste line 135 is coupled to the second end 107 of the flow cell 105 in order to receive waste fluid 138 (i.e., the combination of sheath fluid and the sample stream 123) upon exiting the flow cell 105. A waste pump 140 is in fluid communication with the waste line 135 to help advance the fluid 138 through the waste lines 135 and into a waste fluid reservoir 170 coupled to the second end 137 of the waste line 135.

In one embodiment, the sheath pump 115, the sample pump 130 and/or the waste pump 140 may be various conventional peristaltic pumps. One example peristaltic pump is Gilson Minipuls 3. In one embodiment, the peristaltic pumps may be operated in a manner that reduces pulsatile flow, thereby improving the sample characteristics in the flow cytometer. For example, a tubing length greater than 20 inches between pump and flow cytometer may be used or a linear peristaltic pump such as the Digicare LP5100 may be used to improve the sample characteristics. In one embodiment, the sample fluidic pathway 120, the sheath fluidic pathway 110 and/or the waste line 135 may be made of an elastomer tubing, such as nitrile (NBR), Hypalon, Viton, silicone, polyvinyl chloride ("PVC"), Ethylene-Propylene-Diene-Monomer ("EPDM"), EPDM+ polypropylene, polyurethane or natural rubber, among other possibilities. An example of such a tube may be a polyvinyl chloride (PVC) tube having an inner diameter of about 0.01 to 0.03 inches and a wall thickness of about 0.01 to 0.03 inches. In one embodiment, a preferred tube for a fluidic pathway may be a PVC tube having an inner diameter of about 0.02 inches and a wall thickness of about 0.02 inches.

In addition, the flow cytometer apparatus 100 may include a three-port valve 145 that may be coupled to the waste line 135 between the flow cell 105 and the waste pump 140. The three-port valve 145 may have a first port 146, a second port 147 and a third port 148. The first port 146 of the three-port valve 145 may be arranged in series with the second port 147 such that the first-port 146 is arranged closer to the flow cell 105 than the second port 147. In turn, the third port 148 of the three-port valve 145 may be configured to communicate with atmosphere 149. In normal operation, the third port 148 is closed and waste fluid 138 flows freely through the valve between the first port 146 and the second port 147. As described in more detail with respect to the third aspect of the invention, the third port 148 may be opened upon a detection of a clog to aid in the method for clearing the clog from the flow cytometer apparatus 100.

In one embodiment, the flow cytometer 100 may include a decontamination solution reservoir 150, a cleaning solution reservoir 155 and a cell-compatible fluid reservoir 160 each configured to receive at least a tip of the sample probe 125. Example decontamination solutions that may be provided in the decontamination solution reservoir 150, may include, but are not limited to, a 5.25% concentration of Sodium Hypochlorite to water. Example cleaning solutions that may be provided in the cleaning solution reservoir 155, may include, but are not limited to a 1.5% concentration of Citranox to water.

Further, deionized water may be provided in the cell-compatible fluid reservoir 160. Example cell-compatible fluids that may be provided in reservoir 160 include deionized water, a salt water solution, a buffer, or any other solution with cell-neutral properties. The effect of each of these solutions is discussed in detail with respect to the third aspect of the invention. In a further embodiment, the flow cytometer 100 may also include a back flush waste reservoir 165 configured to receive at least the tip of the sample probe 125. The back flush waste reservoir 165 may receive waste fluids pumped through the flow cytometer apparatus in a reverse-mode as part of a method for clearing a clog from the system. In one embodiment, each of the foregoing reservoirs 150, 155, 160, 165 may be a well that is defined in a well-plate 180. This well-plate 180 may be the same as or different than the well-plate 185 in which the test samples are placed.

Figure 3:
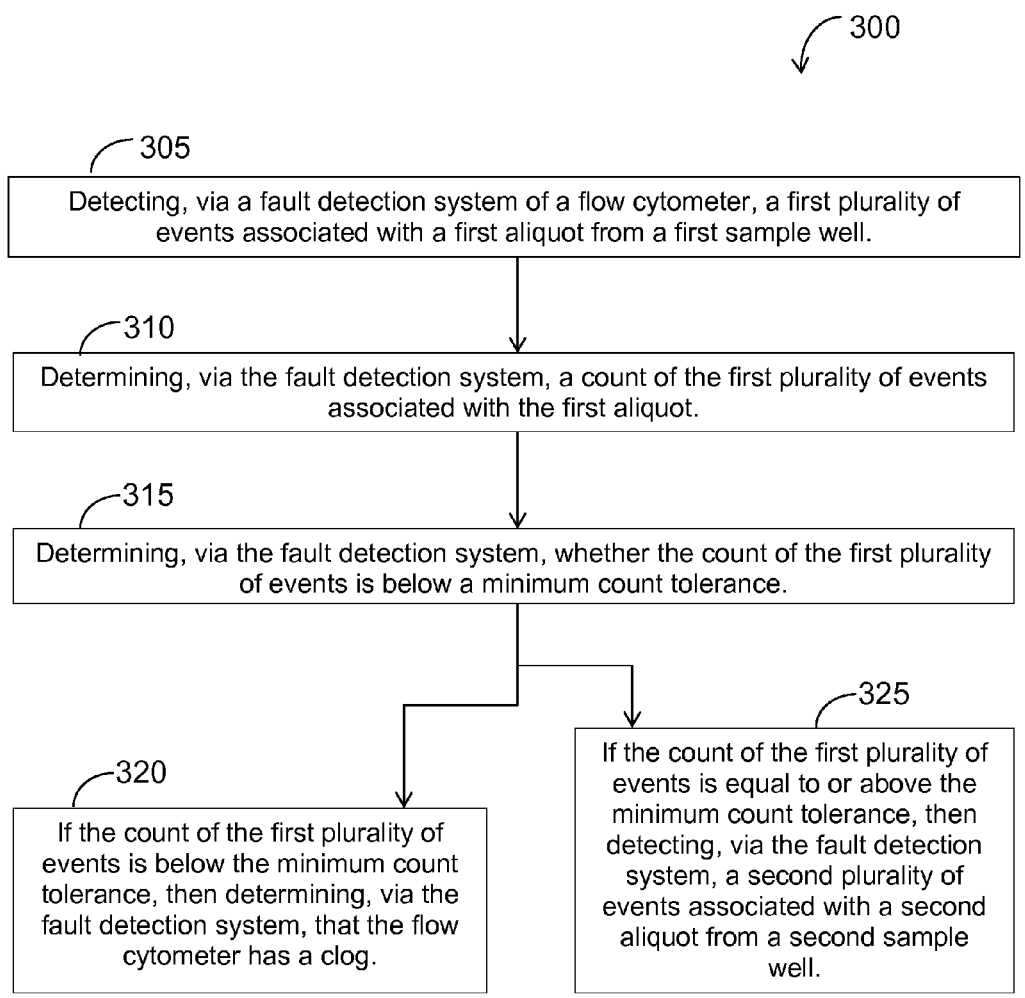
FIG. 3 is a flow chart of a method for detecting a clog in a flow cytometer apparatus, according to one example embodiment.

FIG. 3 is a flow chart of a method 300 for detecting a clog in a flow cytometer, according to one example embodiment. Example methods, such as method 300 of FIG. 3 and method 700 of FIG. 7, may be carried out by an operator or a control system, including the fault detection system. In operation in one example embodiment, high-throughput flow cytometry may use a pump system to fill a sample fluidic pathway 120 with a stream 123 of discrete sample particle suspensions aspirated from one or more wells of a microplate and separated from each other by air gaps. The entire sample stream 123 may be continuously delivered to the flow cell 105 to permit data from each of the samples in the microplate 185 to be acquired and stored in a single data file. During operation, the flow of the sample stream 123 may become interrupted by a clog.

Figure 4:
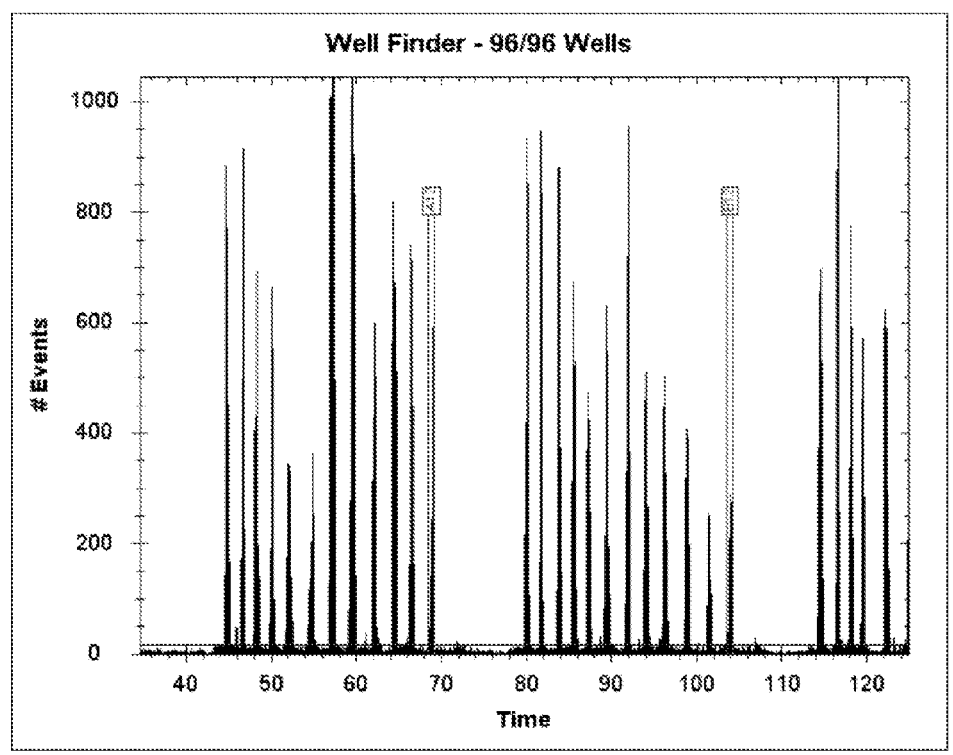
FIG. 4 is a graph showing example event counts over time for a sampled microplate, according to one example embodiment.

As such, in a second aspect, the invention provides a method 300 for detecting a clog in a flow cytometer apparatus of a type known in the art or in a flow cytometer apparatus 100 according to the first aspect of the invention. As shown by block 305, method 300 involves a fault detection system of a flow cytometer 100 detecting a first plurality of events associated with a first aliquot from a first sample well. As used herein, an "event" refers to the presence of one or more particles of interest or marker particles associated with an aliquot of a sample, where the presence may be indicated by physical or chemical features, such as fluorescent intensity of the samples. Then, at block 310, the fault detection system determines a count of the first plurality of events associated with the first aliquot. As used herein, "count" literally refers the number of events detected for a given aliquot of a sample. FIG. 4 reflects data from a typical microplate sample set that provides an example of a plurality of events plotted against time during the course of sampling and data acquisition operations of the flow cytometer apparatus 100. The spikes in the graph represent individual sample wells and the larger low event count gaps between a microplate row or column represents a microplate shake and/or a sample probe rinse. Next, at block 315, the fault detection system determines whether the count of the first plurality of events is below a minimum count tolerance. And, if the count of the first plurality of events is below the minimum count tolerance, then at block 320 the fault detection system determines that the flow cytometer has a clog. If the count of the first plurality of events is equal to or above the minimum count tolerance, then at block 325 the fault detection system detects a second plurality of events associated with a second aliquot from a second sample well thereby continuing a normal sampling operation.

In one embodiment, the fault detection system may include a control system that may take the form of program instructions stored on a non-transitory computer readable medium and a processor that executes the instructions. However, a control system may take other forms including software, hardware, and/or firmware. The fault detection system may be part of or include the data processing system of the flow cytometer or the fault detection system may be a processor that is separate from that of the flow cytometer.

In one embodiment, method 300 may further involve the fault detection system determining a count of the second plurality of events. Then the fault detection system may determine whether the count of the second plurality of events is below a minimum count tolerance. And, if the count of the second plurality of events is below the minimum count tolerance, the fault detection system then may determine that the flow cytometer has a clog. On the other hand, if the count of the second plurality of events is equal to or above the minimum count tolerance, then the fault detection system may detect a third plurality of events associated with a third aliquot from a third sample well of the flow cytometer thereby continuing a normal sampling operation.

In one embodiment, the first aliquot may include a plurality of particles of interest such that the first plurality of counts corresponds to the plurality of particles of interest.

In one embodiment, the count tolerance may be a minimum of fifteen events per second. In various embodiments, the sampling protocol may be analyzed to determine the longest period of time the sample probe may be immersed in one of the decontamination, cleaning or cell-compatible fluid reservoirs during the plate sampling operation. This information may then be entered into the fault detection system so that the fault detection system sets the longest time period during which the fault detection system may expect event counts to be below fifteen events per second. In one embodiment, an additional three seconds may be added to this immersed time period. If the sampling protocol does not include any probe rinses or well-plate shaking, then the longest time period during which the fault detection system may expect event counts to be below fifteen events per second is defaulted to five seconds.

Figure 5:
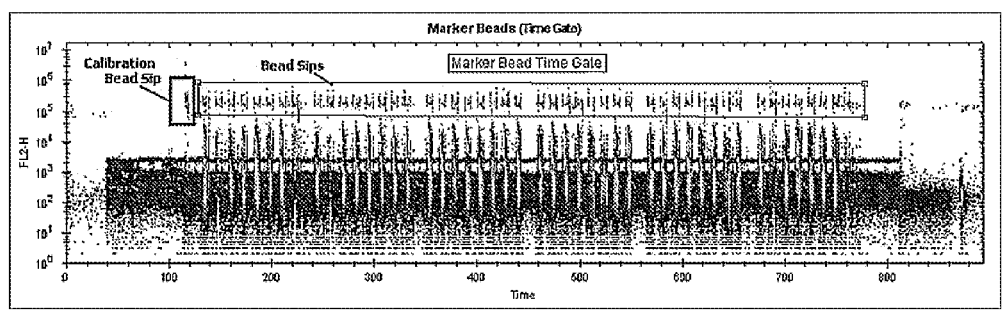
FIG. 5 is a graph showing an initial calibration of the clog detection system with inter-well fluorescent bead sips with a fixed time interval and subsequent inter-well fluorescent bead sips measured in real-time with respect to a user-defined microplate sampling protocol.
Figure 6:
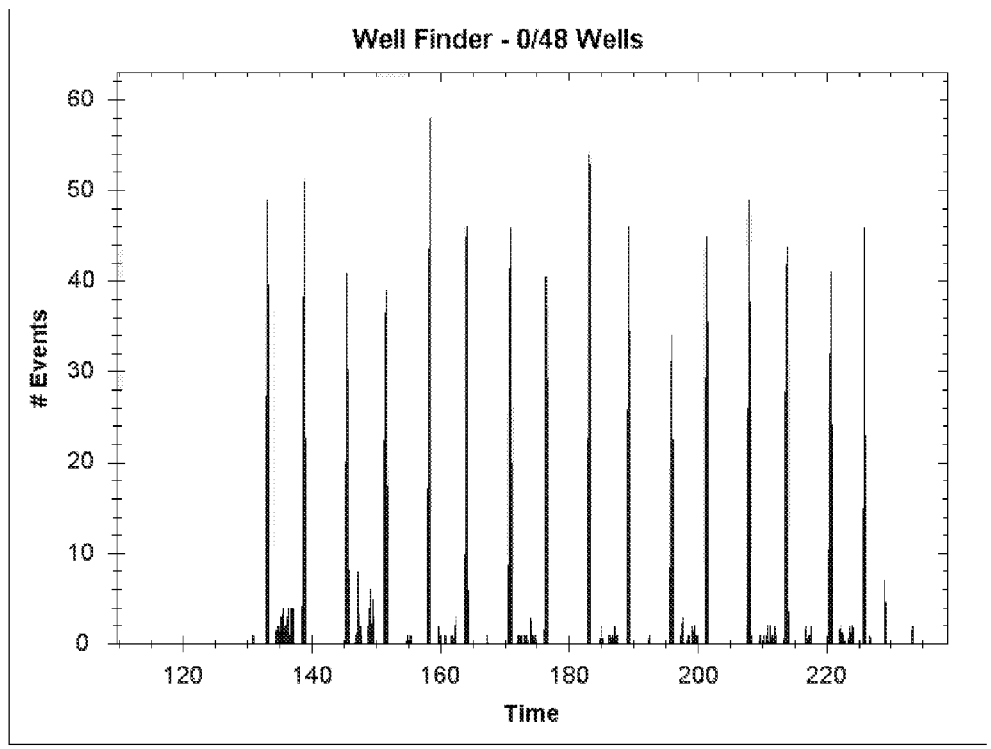
FIG. 6 is a graph showing fluorescent bead sip counts over time.

In a further embodiment, before determining whether the count of the first plurality of events is below a minimum count tolerance, the fault detection system may detect at least 1500 total events from one or more aliquots of samples from one or more sample wells. This may permit the fault detection system to gather enough data to calibrate the system and to determine time gates discussed in more detail below. In one embodiment, as shown in FIG. 5, an example initial calibration fluorescent bead sip via the sample probe 125 may be performed over a fixed time interval to determine the fluorescent intensity and event count for this sample run. If this initial calibration sip is determined to be below a count tolerance, then the flow cytometer apparatus may be determined to be clogged. If this initial calibration sip is above the count tolerance, then it may be used as a measurement against subsequent bead sips as shown in FIGS. 5 and 6. For example, FIG. 6 shows example data gathered via the fault detection system, monitoring the frequency and event counts for subsequent bead sips via the sample probe 125 in real-time. In one embodiment, the fault detection system is set to expect that the first fluorescent bead sip will be a continuous peak that is least two seconds long. The fault detection system may record the event count of this initial peak and then the fault detection system may determine that future between-well fluorescent bead sips are approximately a half second long and may have an event count that is defined as ((CalibrationSipEventCount*BeadSipTime)/CalibrationSipTime)*0.35. If a bead sip does not meet the sip duration time of a half second or achieve an event count within the expected time duration based on the sampling time duration plus up to two additional seconds, the bead sip may be marked as a missed sip and a potential clog. The fault detection system may be programmed to expect a regular interval of bead sips between wells when the system is sampling a plate without a clog. Therefore, in this embodiment, if a bead sip is missed then the flow cytometer system is determined to be in a clogged state.

In another embodiment, the first aliquot may include a plurality of marker particles such that the first plurality of counts corresponds to the plurality of marker particles of the first aliquot. In addition, the second aliquot may include a plurality of particles of interest such that the second plurality of counts corresponds to the plurality of particles of interest. And, the third aliquot may include a plurality of marker particles such that a third plurality of counts corresponds to the plurality of marker particles of the third aliquot. This arrangement may permit time gates to be established as described in more detail below. In this embodiment, every other well of a well-plate may be filled with samples containing marker particles and the wells therebetween may be filled with samples containing particles of interest.

In another embodiment, method 300 may further involve the fault detection system determining a beginning of a count interval for the second aliquot. Then the fault detection system may determine an end of the count interval for the second aliquot. And the fault detection system may detect the plurality of events associated with the second aliquot during the count interval. This embodiment establishes a window of time in which the fault detection system expects to detect particles. In one embodiment, the step of determining a beginning of a count interval for the second aliquot may include the fault detection system determining data corresponding to a first histogram. This first histogram may be based upon the first plurality of events detected for the plurality of marker particles of the first aliquot over time. Then the fault detection system may determine a first time gate and a second time gate, such that the first time gate corresponds to an earliest detected event in the first histogram and the second time gate corresponds to a latest detected event in the first histogram. The second time gate may then be established as the beginning of the count interval. In another embodiment, the step of determining an end of the count interval for the second aliquot may include the fault detection system determining data corresponding to a second histogram. This second histogram may be based upon the third plurality of events detected for the plurality of marker particles of the third aliquot over time. Next, the fault detection system may determine a third time gate and a fourth time gate, such that the third time gate corresponds to an earliest detected event in the second histogram and the fourth time gate corresponds to a latest detected event in the second histogram. The third time gate may then be established as the end of the count interval. In a further embodiment, the fourth time gate may be established as the beginning of a second count interval for a fourth aliquot.

In one embodiment, method 300 may further include the fault detection system determining whether the count of the first plurality of events is above a maximum count tolerance. And, if the count of the first plurality of events is above a maximum count tolerance, then the fault detection system may determine that there is a system anomaly in the flow cytometer. In response to determining the presence of a system anomaly, the fault detection system may pause the sampling operation of the flow cytometer. If, however, the count of the first plurality of events is equal to or below a maximum count tolerance, then the fault detection system detects the second plurality of events associated with the second aliquot from the second sample well of the flow cytometer.

In one embodiment, the step of the fault detection system determining that the flow cytometer has a clog may include the fault detection system detecting at least one more plurality of events associated with a subsequent aliquot in a fluidic pathway of the flow cytometer. Then the fault detection system may determine whether the count of the at least one more plurality of events is below the minimum count tolerance. If the count of the at least one more plurality of events is below the minimum count tolerance, then the fault detection system may pause a sampling operation of the flow cytometer. On the other hand, if the count of the first plurality of events is equal to or above the minimum count tolerance, then the sampling operation of the flow cytometer may continue. This embodiment may permits the flow cytometer system to continue the sampling operation for a certain amount of time after determining a count is below the count tolerance in order to confirm that the low count was not due to a sampling error or due to a chemical reaction diminishing the number of particles present in a given sample.

In another embodiment, the method 300 may further include the fault detection system detecting a fourth plurality of events associated with a fourth aliquot from a fourth sample well of the flow cytometer. Then the fault detection system may determine a count of the fourth plurality of events. Next, the fault detection system may determine whether the count of the fourth plurality of events is below a minimum count tolerance. If the count of the fourth plurality of events is below the minimum count tolerance, then the fault detection system may determine whether the counts of the first, second and third plurality of events were dropped over time such that the counts trended downward. In this case, if the counts of the first, second and third plurality of events dropped over time, then the fault detection system may determine that the flow cytometer has a clog and then may pause a sampling operation of the flow cytometer. Alternatively, if the counts of the first, second and third plurality of events did not drop over time, then the fault detection system may continue the sampling operation of the flow cytometer for at least one more aliquot. In this embodiment, the fault detection system is allowed to assess whether a downward trend in counts was present leading up to the count that did not meet the count tolerance. This may have the benefit of preventing the sample probe from taking up further samples that would go to waste if clog remediation steps are undertaken.

In one embodiment, the first plurality of events may include a plurality of events related to fluorescence of a plurality of particles in the first aliquot. In a further embodiment, the plurality of particles in the first aliquot may be configured to fluoresce in the presence of light of a predetermined frequency. In this embodiment, the flow cytometer may include a laser configured to emit light of the predetermined frequency. The flow cytometer may also be configured to shine light emitted from the laser on the plurality of particles. Then the step of detecting a plurality of events may include detecting an event related to fluorescence of the plurality of particles. In various other embodiments, other events that may be detected are cellular, chemical and protein aggregates or debris.

In one embodiment, method 300 may further include the provision of a flow cytometer system according to the first aspect of the invention. Then, in response to determining that the flow cytometer has a clog, the fault detection system may activate the waste pump, thereby applying negative pressure to one or more of a waste line, a flow cell and a sample fluidic pathway. And a sample pump may also be activated by the fault detection system. Then the flow cytometer system may cycle the sample probe into and out of a decontamination solution reservoir such that a decontamination fluid may be driven by the sample pump through one or more of the flow cell, the sample fluidic pathway and the waste line, thereby clearing a clog.

In a further embodiment, the flow cytometer system may cycle the sample probe into and out of a cleaning solution reservoir. Then the sample pump may drive a cleaning fluid through one or more of the flow cell, the sample fluidic pathway or the waste line, thereby cleaning away the decontamination fluid.

In a still further embodiment, the method 300 may also include the flow cytometer system cycling the sample probe into and out of a cell-compatible fluid reservoir. Then sample pump may drive a cell-compatible fluid through one or more of the waste line, the flow cell and the sample fluidic pathway, thereby removing any remaining cleaning fluid.

Figure 7:
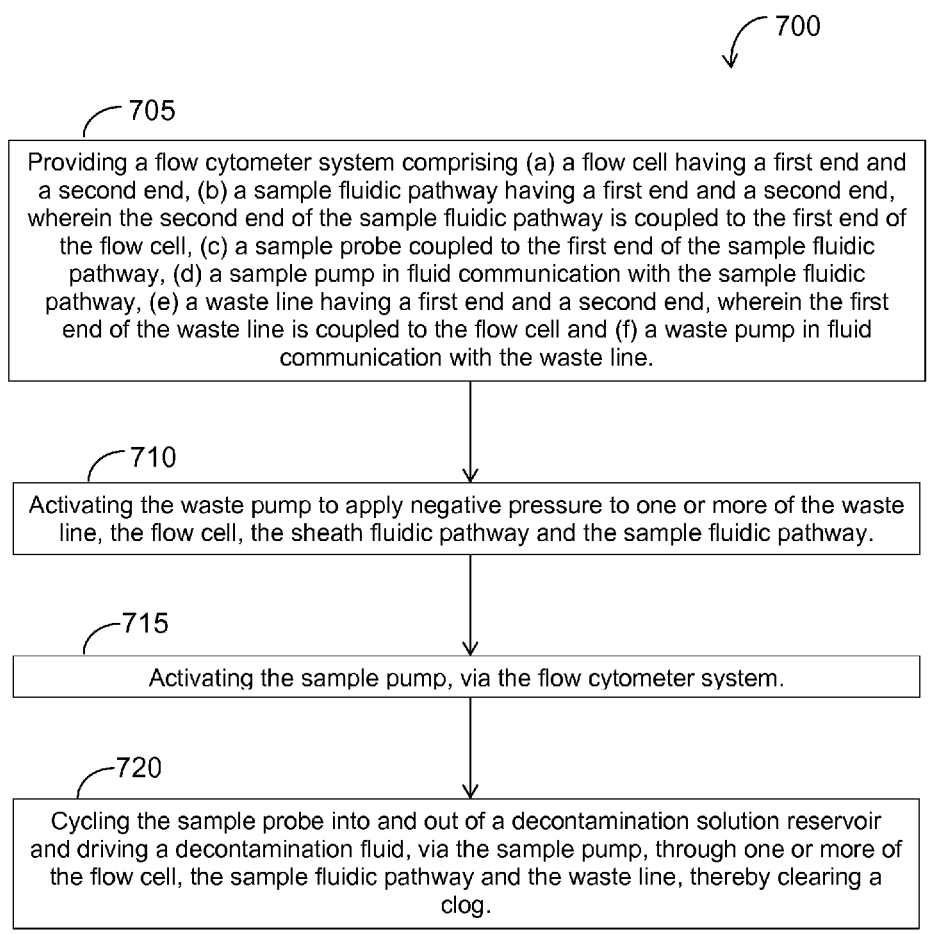
FIG. 7 is a flow chart of a method for clearing a clog from a flow system, according to one example embodiment.

In another embodiment, the method 300 may further include the provision of a sheath fluidic pathway coupled to the first end of the flow cell and a sheath pump in fluid communication with the sheath fluidic pathway. The flow cytometer system may activate the sheath pump, which may then drive a sheath fluid through one or more of the sheath fluidic pathway, the flow cell and the waste line. In a third aspect, the invention provides a method for clearing a clog from the flow cytometer apparatus 100 according to the first aspect of the invention. As shown in FIG. 7, at block 705, a flow cytometer apparatus 100 is provided according to the first aspect of the invention. Then, at block 710, the waste pump 140 is activated to apply negative pressure to one or more of the waste line 135, the flow cell 105 and the sample fluidic pathway 120. The sample pump 130 is activated, at block 715. At block 720, the sample probe 125 cycles into and out of a decontamination solution reservoir 150 and drives a decontamination fluid, via the sample pump 130, through one or more of the flow cell 105, the sample fluidic pathway 120 and the waste line 135, thereby clearing a clog.

In a further embodiment, method 700 may include the sample probe 125 cycling into and out of a cleaning solution reservoir 155. Then a cleaning fluid may be driven via the sample pump 130, through one or more of the flow cell 105, the sample fluidic pathway 120 or the waste line 135, thereby cleaning away the decontamination fluid.

In another embodiment, method 700 may include the sample probe 125 may cycle into and out of a cell-compatible fluid reservoir 160. Then a cell-compatible fluid may be driven through one or more of the waste line 135, the flow cell 105 and the sample fluidic pathway 120, thereby removing any remaining cleaning fluid.

In one embodiment, the method 700 may further include activating the sheath pump 115 and driving a sheath fluid 111 through one or more of the sheath fluidic pathway 110, the flow cell 105 and the waste line 135. The flowing sheath fluid 111 may further aid in flushing the clog, cleaning and/or removing cleaning solution from the flow cell 105 and/or waste line 135 (and/or the sample fluidic pathway 120, if the flow cytometer apparatus 100 is operated in reverse mode).

In one embodiment, cycling of the sample probe 125 into and out of the decontamination solution reservoir 150 may occur for a period of time ranging from about two minutes to about five minutes. In a further embodiment, each cycle of the sample probe 125 into and out of the decontamination solution reservoir 150 may involve placing at least the tip of the sample probe 125 into the decontamination solution reservoir 150 for at least one second and, more preferably, between about one second to about 5 seconds and removing the tip of the sample probe 125 from the decontamination solution reservoir 150 for at least one second and, more preferably, between about one second to about 5 seconds. In another embodiment, the method 700 may include pumping a plurality of decontamination fluid samples separated by air samples through the sample fluidic pathway 120 during the cycling of the sample probe 125 into and out of the decontamination solution reservoir 150. The length or amount of the decontamination fluid samples and the air samples are determined by the amount of time the sample probe spends immersed in decontamination fluid and immersed in atmosphere, respectively. The provision of air samples (i.e. air gaps) in between samples of decontamination fluid proved more effective than continuously pulling decontamination fluid into the sample fluidic pathway 120. The same results are applicable for the cycling of the cleaning solution and the deionized water.

In a further embodiment, the method 700 may also include pumping a plurality of cleaning fluid samples separated by air samples through at least the sample fluidic pathway 120 during the cycling of the sample probe 120 into and out of the cleaning solution reservoir 155. In another embodiment, the sample probe 125 may be cycled into and out of the cleaning solution reservoir 155 for a period of time ranging from about two minutes to about five minutes.

In a further embodiment, each cycle of the sample probe 125 into and out of the cleaning solution reservoir 155 may involve placing at least the tip of the sample probe 125 into the cleaning solution reservoir 155 for about one second to about 5 seconds and removing the tip of the sample probe 125 from the cleaning solution reservoir 155 for about one second to about 5 seconds. In a still further embodiment, the sample probe 125 may be cycled into and out of the cleaning solution reservoir 155 at least 30 times.

In another embodiment, method 700 may include pumping a plurality of deionized water samples separated by air samples through at least the sample fluidic pathway 120 during the cycling of the sample probe 125 into and out of the deionized water reservoir 160. In another embodiment, the sample probe 125 may be cycled into and out of the deionized water reservoir 160 for a period of time ranging from about two minutes to about five minutes. In a further embodiment, each cycle of the sample probe 125 into and out of the deionized water reservoir 160 may involve placing at least the tip of the sample probe 125 into the cell-compatible fluid reservoir 160 for at least one second and, more preferably, between about one second to about 5 seconds and removing the tip of the sample probe 125 from the deionized water reservoir 160 for at least one second and, more preferably, between about one second to about 5 seconds. In a still further embodiment, the sample probe 125 may be cycled into and out of the cell-compatible fluid reservoir 160 at least 30 times.

In one embodiment, prior to activating the waste pump 140, a sampling operation and a data acquisition operation may be ceased. The sampling and data acquisition operations may be ceased in response to a fault detection system determining a clog is present in the flow cytometer apparatus, for example.

In one embodiment, cycling the sample probe 125 into and out of the decontamination solution reservoir 150 may involve: (a) operating the flow cytometer system 100 in a forward mode, (b) deactivating the waste pump 140 and the sample pump 130, (c) holding a plurality of decontamination fluid samples separated by air samples in at least the sample fluidic pathway 120, (d) closing the second port 147 of the three-port valve 145 and opening the third port 148 of the three-port valve 145, (e) operating the sample pump 130 in a reverse-mode and flowing the plurality of decontamination fluid samples in reverse through at least the sample fluidic pathway 120. Operating in reverse mode may be helpful in dislodging a clog if the clog does not clear while operating in a forward mode. In addition, holding the decontamination fluid in contact with the clog for a period of time may help breakdown the clog down.

In another embodiment, cycling the sample probe 125 into and out of the decontamination solution reservoir 150 may involve: (a) operating the flow cytometer system 100 in a forward mode, (b) deactivating the waste pump 140 and the sample pump 130, (c) holding a plurality of decontamination fluid samples separated by air samples in at least the sample fluidic pathway 120, (d) operating the sample pump 130 in the forward-mode and flowing the plurality of decontamination fluid samples through the three-port valve 145 and into the waste reservoir 170.

In one embodiment, cycling the sample probe 125 into and out of the cleaning solution reservoir 155 may involve: (a) operating the flow cytometer system 100 in the forward mode, (b) deactivating the waste pump 140 and the sample pump 130, (c) holding a plurality of cleaning fluid samples separated by air samples in the sample fluidic pathway 120, (d) closing the second port 147 of the three-port valve 145 and opening the third port 148 of the three-port valve 145 (e) operating the sample pump 130 in the reverse-mode and flowing the plurality of decontamination fluid samples in reverse through at least the sample fluidic pathway 120.

In another embodiment, cycling the sample probe 125 into and out of the cleaning solution reservoir 155 may involve: (a) operating the flow cytometer system 100 in the forward mode, (b) deactivating the waste pump 140 and the sample pump 130, (c) holding a plurality of cleaning fluid samples separated by air samples in the sample fluidic pathway 120, (d) operating the sample pump 130 in the forward-mode and flowing the plurality of decontamination fluid samples through the three-port valve 145 and into the waste reservoir 170.

In a still further embodiment, cycling the sample probe 125 into and out of the cell-compatible fluid reservoir 160 may involve: (a) activating the sheath pump 115 and (b) operating the flow cytometer system 100 in the forward mode. This may have the benefit of flushing any decontamination fluid or cleaning fluid that may have backed up into the sheath fluidic pathway 110.

In another embodiment, the sample probe 125 may be positioned over a back flush waste fluid reservoir 165 when the sample pump 130 is operating in a reverse-mode. In operation, the back flush waste fluid reservoir 165 may receive decontamination fluid, cleaning solution and/or cell-compatible fluid after theses fluids have been flushed through various components of the flow cytometer 100 as described in the foregoing embodiments.

The above detailed description describes various features and functions of the disclosed flow cytometer apparatus and methods for detecting and/or clearing of a clog in the flow cytometer apparatus with reference to the accompanying figures. While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All embodiments of the flow cytometer apparatus may be used in the methods of the second and third aspects of the invention. Note that any of the foregoing embodiments of any aspect may be combined together to practice the claimed invention unless the context dictates otherwise.

The invention claimed is:

1. A method, comprising:
providing a flow cytometer system comprising (a) a flow cell having a first end and a second end, (b) a sample fluidic pathway having a first end and a second end, wherein the second end of the sample fluidic pathway is coupled to the first end of the flow cell, (c) a sample probe coupled to the first end of the sample fluidic pathway, (d) a sample pump in fluid communication with the sample fluidic pathway, (e) a waste line having a first end and a second end, wherein the first end of the waste line is coupled to the flow cell and (f) a waste pump in fluid communication with the waste line;
activating the waste pump to apply negative pressure to one or more of the waste line, the flow cell, the sheath fluidic pathway and the sample fluidic pathway;
activating the sample pump;
cycling the sample probe into and out of a decontamination solution reservoir and driving a decontamination fluid, via the sample pump, through one or more of the flow cell, the sample fluidic pathway and the waste line, thereby clearing a clog, wherein cycling the sample probe into and out of the decontamination solution reservoir occurs for a period of time ranging from about two minutes to about five minutes.

2. The method of claim 1, further comprising:
cycling the sample probe into and out of a cleaning solution reservoir; and
driving a cleaning fluid, via the sample pump, through one or more of the flow cell, the sample fluidic pathway or the waste line, thereby cleaning away the decontamination fluid.

3. The method of claim 2, further comprising:
cycling the sample probe into and out of a cell-compatible fluid reservoir; and
driving cell-compatible fluid through one or more of the waste line, the flow cell and the sample fluidic pathway, thereby removing any remaining cleaning fluid.

4. The method of claim 3, further comprising:
during the cycling of the sample probe into and out of the cell-compatible fluid reservoir, pumping a plurality of cell-compatible fluid samples separated by air samples through at least the sample fluidic pathway.

5. The method of claim 2, further comprising:
during the cycling the sample probe into and out of the cleaning solution reservoir, pumping a plurality of cleaning fluid samples separated by air samples through at least the sample fluidic pathway.

6. The method of claim 3, wherein cycling the sample probe into and out of the cell-compatible fluid reservoir occurs for a period of time ranging from about two minutes to about five minutes.

7. The method of claim 2, wherein cycling the sample probe into and out of the cleaning solution reservoir occurs for a period of time ranging from about two minutes to about five minutes.

8. The method of claim 1, further comprising:
providing a sheath fluidic pathway coupled to the first end of the flow cell and a sheath pump in fluid communication with the sheath fluidic pathway;
activating the sheath pump; and
driving a sheath fluid through one or more of the sheath fluidic pathway, the flow cell and the waste line.

9. The method of claim 1, further comprising:
during the cycling of the sample probe into and out of the decontamination solution reservoir, pumping a plurality of decontamination fluid samples separated by air samples through the sample fluidic pathway.

10. The method of claim 1, further comprising:
prior to activating the waste pump, ceasing a sampling operation and a data acquisition operation.

11. The method of claim 1, further comprising:
providing a three-port valve coupled to the waste line between the flow cell and the waste pump, wherein the three-port valve has a first port, a second port and a third port, wherein the first port of the three-port valve is arranged in series with the second port of the three-port valve such that the first-port is arranged closer to the flow cell than the second port, and wherein the third port of the three-port valve is configured to communicate with atmosphere; and
wherein cycling the sample probe into and out of the decontamination solution reservoir comprises:
(a) operating the flow cytometer system in a forward mode;
(b) deactivating the waste pump and the sample pump;
(c) holding a plurality of decontamination fluid samples separated by air samples in at least the sample fluidic pathway;
(d) closing the second port of the three-port valve and opening the third port of the three-port valve;
(e) operating the sample pump in a reverse-mode and flowing the plurality of decontamination fluid samples in reverse through at least the sample fluidic pathway.

12. The method of claim 11, further comprising cycling the sample probe into and out of a cleaning solution reservoir, wherein cycling the sample probe into and out of the cleaning solution reservoir comprises:
(a) operating the flow cytometer system in the forward mode;
(b) deactivating the waste pump and the sample pump;
(c) holding a plurality of cleaning fluid samples separated by air samples in the sample fluidic pathway;
(d) closing the second port of the three-port valve and opening the third port of the three-port valve; and
(e) operating the sample pump in the reverse-mode and flowing the plurality of decontamination fluid samples in reverse through at least the sample fluidic pathway.

13. The method of claim 12, further comprising cycling the sample probe into and out of a cell-compatible fluid reservoir, wherein cycling the sample probe into and out of the cell-compatible fluid reservoir comprises:
(a) activating the sheath pump; and
(b) operating the flow cytometer system in the forward mode.

14. The method of claim 1, wherein the sample probe is positioned over a back flush waste fluid reservoir when the sample pump is operating in a reverse-mode.

* * * * *